US011572554B2

(12) United States Patent
Huang et al.

(10) Patent No.: US 11,572,554 B2
(45) Date of Patent: Feb. 7, 2023

(54) TARGET IRRELEVANT GUIDE RNA FOR CRISPR

(71) Applicant: Siemens Healthcare GmbH, Erlangen (DE)

(72) Inventors: Yiwei Huang, Erlangen (DE); Maximilian Würstle, Baiersdorf (DE); Tivadar Mach, Nuremberg (DE); Stefan Prause, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 5 days.

(21) Appl. No.: 17/292,023

(22) PCT Filed: Oct. 29, 2019

(86) PCT No.: PCT/EP2019/079478
§ 371 (c)(1),
(2) Date: May 7, 2021

(87) PCT Pub. No.: WO2020/094456
PCT Pub. Date: May 14, 2020

(65) Prior Publication Data
US 2021/0355482 A1 Nov. 18, 2021

(30) Foreign Application Priority Data
Nov. 7, 2018 (EP) .................................... 18204790

(51) Int. Cl.
*C12Q 1/68* (2018.01)
*C12Q 1/6806* (2018.01)
*C12N 15/11* (2006.01)
*C12N 15/10* (2006.01)

(52) U.S. Cl.
CPC ...... *C12N 15/1058* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2015/0225773 A1* | 8/2015 | Farmer | ............... C12N 15/1003 506/26 |
| 2016/0017396 A1 | 1/2016 | Cann et al. | |
| 2016/0362680 A1 | 12/2016 | Armour et al. | |
| 2018/0051320 A1 | 2/2018 | DeRisi et al. | |
| 2018/0298421 A1 | 10/2018 | Carpenter et al. | |

OTHER PUBLICATIONS

Hybridization probe—Wikipedia; pp. 1-4; downloaded Jan. 24, 2022.*
Cong, Le et al.: "Multiplex Genome Engineering Using CRISPR/Cas Systems"; in: Science; vol. 339; pp. 819-823; 2013.
Feng, Yanxiao et al.: "Nanopore-based Fourth-generation DNA Sequencing Technology"; in: Genomics Proteomics Bioinformatics; vol. 13; pp. 4-16; 2015.
Goodwin, Sara et al.: "Coming of age: ten years of next generation sequencing technologies"; in: Nature Reviews Genetics; vol. 17, pp. 333-351; 2016.
Gu, W. et al.: "Depletion of Abundant Sequences by Hybridization (DASH): using Cas9 to remove unwanted high-abundance species in sequencing libraries and molecular counting applications"; in: Genome Biology; vol. 17; No. 41; 2016.
Jiang, Fuguo and Doudna, Jennifer A.: "CRISPR-Cas9 Structures and Mechanisms."; in: Annual Review of Biophysics; vol. 46; pp. 505-529; 2017.
Jinek, Martin et al.: "A Programmable Dual-RNA-Guided DNA Endonuclease in Adaptive Bacterial Immunity"; in: Science; vol. 337; pp. 816-821; 2012.
Lee, Dong-Hoon et al.: "A structural determinant in the uracil DNA glycosylase superfamily for the removal of uracil from adenine/uracil base pairs"; in: Nucleic Acids Research; vol. 43; No. 2; 2018.
Makarova, Kira S. et al.: "Unification of Cas protein families and a simple scenario for the origin and evolution of CRISPR-Cas systems"; in: Biology Direct; vol. 6; No. 38; 2011.
Mertes, Florian et al.: "Targeted enrichment of genomic DNA regions for next-generation sequencing"; in: Briefings in Functional Genomics; vol. 10; No. 6; pp. 374-386; 2011.
Milligan, John F. et al.: "Oligoribonucleotide synthesis using T7 RNA polymerase and synthetic DNA templates."; in: Nucleic Acids Research; vol. 15; No. 21; pp. 8783-8798; 1987.
Nowak, Chance M. et al.: "Guide RNA engineering for versatile Cas9 functionality"; in: Nucleic Acids Research; vol. 44; No. 20; pp. 9555-9564; 2016.
Van Dijk, Erwin L. et al.: "Ten years of next-generation sequencing technology"; in: Trends in Genetics; vol. 30; No. 9; pp. 418-426; 2014.
Wang, Haifeng et al.: "CRISPR/Cas9 in Genome Editing and Beyond"; in: Annual Review of Biochemistry; vol. 85; pp. 22.1-22.38; 2016.
Domingues, "PCR Methods and Protocols" 2017, ed. Lucilia Domingues, in Methods in Molecular Biology, Series Editor: John Walker, Springer, New York; 2017, p. 1-283.
Lee et al., "Highly efficient CRISPR/Cas9-mediated TAR cloning of genes and chromosomal loci from complex genomes in yeast", Nucleic Acids Research, 2015, vol. 43, No. 8 e55, S. 1-9.
McClelland and Welsh, 1994, PCR Methods Appl., 4: S59-65.
Zheng et al, "Titration-free massively parallel pyrosequencing using trace amounts of starting material", Nucleic Acids Research, 2010, vol. 38, No. 13, e137, pp. 1-9.

* cited by examiner

*Primary Examiner* — Maria G Leavitt
(74) *Attorney, Agent, or Firm* — BakerHostetler

(57) ABSTRACT

The present invention relates to a method of obtaining an enriched population of a target polynucleotide using a synthetic single guide RNA (sgRNA) for an sgRNA-guided nucleic acid-binding protein, as well as to a method of obtaining a pool of target-irrelevant synthetic single guide RNAs (sgRNAs) for a sgRNA-guided nucleic acid-binding protein. Also provided is a target polynucleotide and sgRNAs obtainable by the methods of the invention. Further envisaged is a kit comprising a pool of sgRNAs obtainable by the method of the invention, and the use of a pool of sgRNAs obtainable by the methods of the invention.

28 Claims, 2 Drawing Sheets

TARGET IRRELEVANT GUIDE RNA FOR CRISPR

CROSS-REFERENCE TO RELATED APPLICATIONS

This application is a 35 U.S.C. § 371 national phase application of International Patent Application No. PCT/EP2019/079478, filed Oct. 29, 2019, which claims priority to EP Application No. 18204790.2, filed Nov. 7, 2018, the entire disclosure of each of which is incorporated herein by reference in its entirety.

TECHNICAL FIELD

The present invention relates to a method of obtaining an enriched population of a target polynucleotide using a synthetic single guide RNA (sgRNA) for an sgRNA-guided nucleic acid-binding protein, as well as to a method of obtaining a pool of target-irrelevant synthetic single guide RNAs (sgRNAs) for a sgRNA-guided nucleic acid-binding protein. Also provided is a target polynucleotide and sgRNAs obtainable by the methods of the invention. Further envisaged is a kit comprising a pool of sgRNAs obtainable by the methods of the invention, and the use of a pool of sgRNAs obtainable by the methods of the invention.

BACKGROUND

Next-generation sequencing (NGS) is a major driver in genetics and molecular research, including modern diagnostics inter alia in the field of cancer medicine. The technology provides a powerful way to study DNA or RNA samples. New and improved methods and protocols have been developed to support a diverse range of applications, including the analysis of genetic variations and sample specific differences. To improve this approach, methods have been developed that aim at a targeted enrichment of sequencing libraries by focusing on specific sequences, transcripts, genes or genome sub-regions, or by eliminating undesirable sequences.

Targeted enrichment can be useful in a number of situations where, for example, particular portions of a whole genome need to be analyzed. The efficient sequencing of a complete exome (all transcribed sequences) is a typical example for this approach. Further examples include the enrichment of specific transcripts, the enrichment of mutation hotspots or the exclusion of disturbing nucleic acid species.

Current techniques for targeted enrichment include (i) Hybrid capture, wherein nucleic acid strands derived from the input sample are hybridized specifically to pre-prepared DNA fragments complementary to the targeted regions of interest, either in solution or on a solid support, so that one can physically capture and isolate the sequences of interest; (ii) Selective circularization or molecular inversion probes (MIPs), wherein single-stranded DNA circles that include target region sequences are formed by gap-filling and ligation chemistries in a highly specific manner, creating structures with common DNA elements that are then used for selective amplification of the targeted regions of interest; and (iii) Polymerase Chain Reaction (PCR) amplification, wherein PCR is directed toward the targeted regions of interest by conducting multiple long-range PCRs in parallel, a limited number of standard multiplex PCRs or highly multiplexed PCR methods that amplify very large numbers of short fragments (Mertes et al., 2011, Briefings in functional Genomics, 10, 6, 374-386).

More recently, the CRISPR/Cas-technology was used for targeted enrichment purposes, in particular in order to remove unwanted sequences from a sequencing library.

The CRISPR/Cas-technology is a new and very versatile genome- and epigenome-editing tool based on repurposing the CRISPR/Cas (clustered regularly interspersed short palindromic repeats/Cas) bacterial immune system (Cong et al, 2013, Science, 339, 819-824). The Cas nuclease, when complexed with a short RNA oligonucleotide known as a single guide RNA (sgRNA), can induce double-stranded breaks (DSBs) at specific sgRNA complementary locations. The CRISPR/Cas system has further been repurposed as a programmable restriction enzyme to direct cleavage in a very precise and customized manner (Lee et al., 2015, Nucleic Acids Res., 43, 1-9).

Accordingly, methods using CRISPR/Cas have been developed which selectively deplete overabundant sequences in a process termed Depletion of Abundant Sequences by Hybridization (DASH). DASH was used to remove targets such as ribosomal RNA (rRNA) from mRNA-seq and wild-type KRAS background sequence from cancer samples by directing their targeted cleavage and preventing their further amplification and sequencing (Gu et al., 2016. Genome Biol., 17, 41). According to Gu et al., employing DASH after transposon-mediated fragmentation but prior to the following amplification step (which relies on the presence of adaptor sequences on both ends of the fragment) is capable of preventing amplification of the targeted sequences (mitochondrial rRNA), thereby ensuring they are not represented in the final sequencing library.

However, this enrichment approach is suitable to remove only a specific species from the sequencing library, while all other sequences remain in the library. There is hence a need for a streamlined, cost- and resource-sensitive enrichment and sequencing approach, which allows for an efficient reduction of the complexity of the sequencing library and thereby implicates a decreased sequencing depth and a manageable amount of data to be processed.

SUMMARY

The present invention addresses this need and provides a method of obtaining an enriched population of a target polynucleotide comprising: (i) providing a pool of starting oligonucleotides for the preparation of a pool of synthetic single guide RNAs synthetic single guide RNA (sgRNA) for an sgRNA-guided nucleic acid-binding protein, wherein said starting oligonucleotide comprises a promoter segment, a random segment as target specific sequence and a binding segment, which is complementary to at least a portion of a scaffold sequence for interaction with the sgRNA-guided nucleic acid-binding protein; (ii) providing one or more sense and/or antisense strand catcher oligonucleotides, which are complementary to at least a portion of the target specific sequence, comprising a tag capable of binding to a cognate interactor; (iii) hybridizing said pool of starting oligonucleotides and said sense and/or antisense strand catcher oligonucleotide(s); (iv) removing complexes of starting oligonucleotides and sense strand catcher oligonucleotides and/or complexes of starting oligonucleotides and antisense strand catcher oligonucleotides from said pool of starting oligonucleotides by binding said tag to a cognate interactor, preferably located on a bead or a suitable surface, thereby obtaining a reduced pool of starting oligonucleotides; (v) preparing a pool of sgRNAs with said reduced pool of starting oligonucleotides obtained in step (iv); (vi) cleaving a mixture of polynucleotides obtained from a test sample with an sgRNA-guided nucleic acid-binding protein using the pool of sgRNAs obtained in step (v); and (vii) size selecting uncut target polynucleotides from said mixture of polynucleotides obtained in step (vi). The method advantageously allows to remove all sequences which are target-irrelevant via the provision of an sgRNA pool capable of binding to said sequences. Thereby the complexity of the sequencing library is drastically reduced and performing sequencing operations, in particular next generation sequencing (NGS), on the library involves a much lower sequencing depth which significantly reduces the sequencing costs as well as subsequent data management and data processing costs.

In a further aspect the present invention relates to a method of obtaining a pool of target-irrelevant synthetic single guide RNAs (sgRNAs) for a sgRNA-guided nucleic acid-binding protein comprising: (i) providing a pool of starting oligonucleotides for the preparation of a pool of synthetic single guide RNAs synthetic single guide RNA (sgRNA) for an sgRNA-guided nucleic acid-binding protein, wherein said starting oligonucleotide comprises a promoter segment, a random segment as target specific sequence and a binding segment, which is complementary to at least a portion of a scaffold sequence for interaction with the sgRNA-guided nucleic acid-binding protein; (ii) providing one or more sense and/or antisense strand catcher oligonucleotides, which are complementary to at least a portion of the target specific sequence, comprising a tag capable of binding to a cognate interactor; (iii) hybridizing said pool of starting oligonucleotides and said sense and/or antisense strand catcher oligonucleotide(s); (iv) removing complexes of starting oligonucleotides and sense strand catcher oligonucleotides and/or complexes of starting oligonucleotides and antisense strand catcher oligonucleotides from said pool of starting oligonucleotides by binding said tag to a cognate interactor, preferably located on a bead or a suitable surface, thereby obtaining a reduced pool of starting oligonucleotides; and (v) preparing a pool of target-irrelevant sgRNAs with said reduced pool of starting oligonucleotides obtained in step (iv).

In a preferred embodiment of the present invention, the sgRNA-guided nucleic acid-binding protein is a DNA binding Cas protein.

In a particularly preferred embodiment, the DNA binding Cas protein is a member of the family of Cas9 proteins, preferably a Cas9 protein or a derivative thereof.

In a further embodiment said random segment comprises between about 10 to 30 random nucleotides. It is preferred that the random segment comprises about 20 random nucleotides.

In yet another embodiment said catcher oligonucleotide comprises between about 10 to 30 nucleotides. It is preferred that the catcher oligonucleotide comprises 20 nucleotides.

In a further embodiment of the present invention, the tag capable of binding to a cognate interactor is biotin and said cognate interactor is streptavidin.

In another embodiment of the present invention the steps (iii) to (iv) as mentioned above are repeated 1, 2, 3, 4, 5 or more times.

In another embodiment of the present invention said target polynucleotide represents a gene, one or more exons of a gene, an intergenic region, a non-transcribed regulatory region, and/or an open reading frame or a sub-portion thereof; or a panel of different genes, a panel of one or more exons of different genes, a panel of intergenic regions, a panel of non-transcribed regulatory regions, and/or a panel of open reading frames or sub-portions thereof, or any combination of any of the before mentioned elements.

In yet another embodiment the present invention relates to any method as mentioned above, wherein during each repetition of method steps (iii) to (iv) one or more catcher oligonucleotide(s) representing one or more different gene(s), exon(s) or open reading frame(s) are used.

In a further embodiment said mixture of polynucleotides obtained from a test sample as mentioned above comprises genomic DNA and/or cDNA molecules whose size is optionally adjusted to a predefined value.

In yet another preferred embodiment of the present invention said method of obtaining an enriched population of a target polynucleotide as described above additionally comprises as step (viii) a step of sequencing said size selected uncut target polynucleotide(s).

In a further aspect the present invention relates to a target polynucleotide obtainable by the method of obtaining an enriched population of a target polynucleotide as described above. The present invention further relates to a pool of sgRNAs obtainable by the method of obtaining a pool of target-irrelevant synthetic single guide RNAs (sgRNAs) for a sgRNA-guided nucleic acid-binding protein as described above.

In another aspect the present invention relates to a kit comprising a pool of sgRNAs obtainable by the method of obtaining a pool of target-irrelevant synthetic single guide RNAs (sgRNAs) for a sgRNA-guided nucleic acid-binding protein as described above and a sgRNA-guided nucleic acid-binding protein. It is preferred that the sgRNA-guided nucleic acid-binding protein is a Cas9 protein or derivative thereof.

In a final aspect the present invention relates to the use of a pool of sgRNAs obtainable by the method of obtaining a pool of target-irrelevant synthetic single guide RNAs (sgRNAs) for a sgRNA-guided nucleic acid-binding protein as described above for the removal of target-irrelevant polynucleotides from a mixture of polynucleotides in a Cas9-based endonuclease assay.

It is to be understood that the features mentioned above and those yet to be explained below may be used not only in the respective combinations indicated, but also in other combinations or in isolation without departing from the scope of the invention.

DETAILED DESCRIPTION OF EMBODIMENTS

Figure 1:
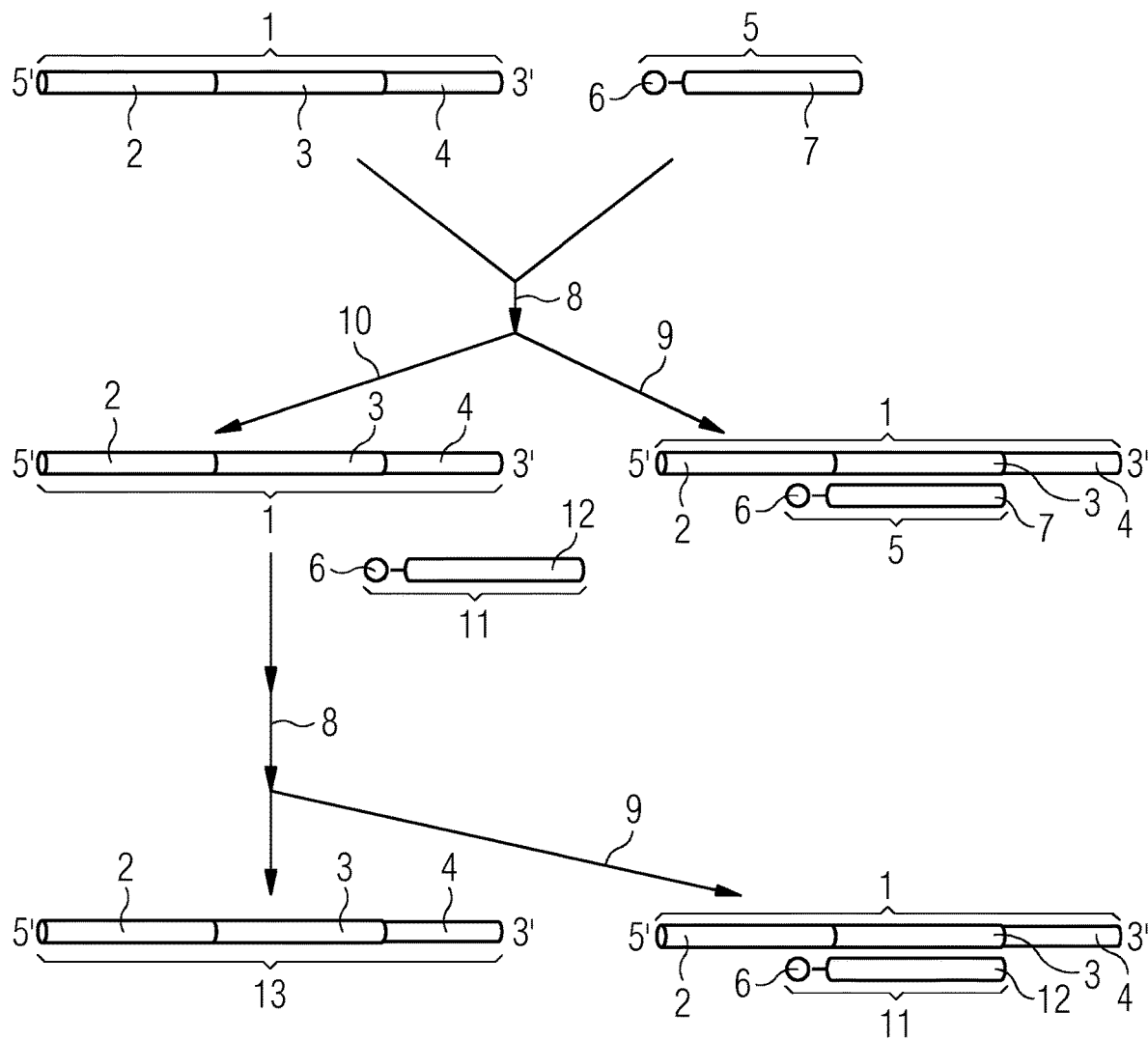
FIG. 1 shows a schematic illustration of the steps for obtaining a pool of target-irrelevant synthetic single guide RNAs (sgRNAs) according to an embodiment of the present invention.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" or "essentially consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "(i)", "(ii)", "(iii)" or "(a)", "(b)", "(c)", "(d)", or "first", "second", "third" etc. and the like in the description or in the claims, are used for distinguishing between similar elements and not necessarily for describing a sequential or chronological order.

It is to be understood that the terms so used are interchangeable under appropriate circumstances and that the embodiments of the invention described herein are capable of operation in other sequences than described or illustrated herein. In case the terms relate to steps of a method, procedure or use there is no time or time interval coherence between the steps, i.e. the steps may be carried out simultaneously or there may be time intervals of seconds, minutes, hours, days, weeks etc. between such steps, unless otherwise indicated.

It is to be understood that this invention is not limited to the particular methodology, protocols etc. described herein as these may vary. It is also to be understood that the terminology used herein is for the purpose of describing particular embodiments only, and is not intended to limit the scope of the present invention that will be limited only by the appended claims.

The drawings are to be regarded as being schematic representations and elements illustrated in the drawings are not necessarily shown to scale. Rather, the various elements are represented such that their function and general purpose become apparent to a person skilled in the art.

Unless defined otherwise, all technical and scientific terms used herein have the same meanings as commonly understood by one of ordinary skill in the art.

As has been set out above, the present invention concerns in one aspect a method of obtaining an enriched population of a target polynucleotide comprising: (i) providing a pool of starting oligonucleotides for the preparation of a pool of synthetic single guide RNAs synthetic single guide RNA (sgRNA) for an sgRNA-guided nucleic acid-binding protein, wherein said starting oligonucleotide comprises a promoter segment, a random segment as target specific sequence and a binding segment, which is complementary to at least a portion of a scaffold sequence for interaction with the sgRNA-guided nucleic acid-binding protein; (ii) providing one or more sense and/or antisense strand catcher oligonucleotides, which are complementary to at least a portion of the target specific sequence, comprising a tag capable of binding to a cognate interactor; (iii) hybridizing said pool of starting oligonucleotides and said sense and/or antisense strand catcher oligonucleotide(s); (iv) removing complexes of starting oligonucleotides and sense strand catcher oligonucleotides and/or complexes of starting oligonucleotides and antisense strand catcher oligonucleotides from said pool of starting oligonucleotides by binding said tag to a cognate interactor, preferably located on a bead or a suitable surface, thereby obtaining a reduced pool of starting oligonucleotides; (v) preparing a pool of sgRNAs with said reduced pool of starting oligonucleotides obtained in step (iv); (vi) cleaving a mixture of polynucleotides obtained from a test sample with an sgRNA-guided nucleic acid-binding protein using the pool of sgRNAs obtained in step (v); and (vii) size selecting uncut target polynucleotides from said mixture of polynucleotides obtained in step (vi).

The term "target polynucleotide" as used herein relates to any nucleic acid molecule of interest, which is amenable to molecular analysis. Preferably, the target polynucleotide is a DNA or cDNA molecule. In specific embodiments of the present invention the target polynucleotide represents a gene, one or more exons of a gene, an intergenic region, a non-transcribed regulatory region, and/or an open reading frame or a sub-portion thereof. In further embodiments, the target polynucleotide may also be a panel of different genes, a panel of one or more exons of different genes, a panel of intergenic regions, a panel of non-transcribed regulatory regions, and/or a panel of open reading frames or sub-portions thereof. Further preferred are combinations of the before mentioned elements. The form and content of the target polynucleotide is typically reflected by the content, sequence and number of catcher oligonucleotides as used in the methods of the present invention.

In a first step of the method of the present invention a pool of starting oligonucleotides for the preparation of synthetic single guide RNA (sgRNA) for an sgRNA-guided nucleic acid-binding protein is provided.

The method is, in general, based on the employment of the CRISPR/Cas system. The term "CRISPR/Cas system" as used herein relates to a biochemical method to specifically cut and modify nucleic acids, also known as genome editing. For example, genes in a genome can generally be inserted, removed or switched off with the CRISPR/Cas system, nucleotides in a gene or nucleic acid molecule can also be changed. The effect of the concept and activity steps of the CRISPR/Cas system has various similarities to that of RNA interference, since short RNA fragments of about 18 to 20 nucleotides mediate the binding to the target in both bacterial defense mechanisms. In the CRSIPR/Cas system typically RNA-guided nucleic acid-binding proteins, such as Cas proteins, bind certain RNA sequences as ribonucleoproteins. For example, a Cas endonuclease (e.g. Cas9, Cas5, Csn1 or Csx12, or derivatives thereof) can bind to certain RNA sequences termed crRNA repeats and cut DNA in the immediate vicinity of these sequences. Without wishing to be bound by theory, it is believed that the crRNA repeat sequence forms a secondary RNA structure and is then bound by the nucleic acid-binding protein (e.g. Cas) which alters its protein folding allowing the target DNA to be bound by the RNA. Furthermore, the presence of a PAM motif, i.e. a protospacer adjacent motif, in the target DNA is necessary to activate the nucleic acid-binding protein (e.g. Cas). The DNA is typically cut three nucleotides before the PAM motif. The crRNA repeat sequence is typically followed by a sequence binding to the target DNA, i.e. a crRNA spacer; both sequences, i.e. the crRNA repeat motif and the target binding segment are usually labelled as "crRNA". This second part of the crRNA (target binding segment) is a crRNA-spacer sequence having the function of a variable adapter. It is complementary to the target DNA and binds to said target DNA. An additional RNA, a tracrRNA, or trans-acting CRISPR RNA, is also required. tracrRNA is partially complementary to crRNA, so that they bind to each other. tracrRNA typically binds to a precursor crRNA, forms an RNA double helix and is converted into the active form by RNase III. These properties allow for a binding to the DNA and a cutting via the endonuclease function of the nucleic acid-binding protein (e.g. Cas) near the binding site.

The term "starting oligonucleotide" as used herein relates to a short nucleic acid molecule or nucleic acid oligomer. Its lengths may vary according to the specific application, targeting approach, genetic background of involved organisms etc. Typically, the length of the starting oligonucleotide is between about 40 and 250 nucleotides, e.g. 40, 45, 50, 55, 60, 65, 100, 150, 200 or 250 nucleotides or any value in between the mentioned values. It is preferred that the length of the oligonucleotide is 55 nucleotides. It is preferred that the starting oligonucleotide is a single strand DNA molecule. Also envisaged, in specific alternative embodiments, are RNA, PNA, CNA, HNA, LNA or ANA molecules or mixtures thereof as starting oligonucleotides. The term "PNA" as used herein relates to a peptide nucleic acid, i.e. an artificially synthesized polymer similar to DNA or RNA. The PNA backbone is typically composed of repeating N-(2-aminoethyl)-glycine units linked by peptide bonds. The various purine and pyrimidine bases are linked to the backbone by methylene carbonyl bonds. The term "CNA" as used herein relates to a cyclopentane nucleic acid, i.e. a nucleic acid molecule comprising for example 2'-deoxycarbaguanosine. The term "HNA" relates to hexitol nucleic acids, i.e. DNA analogues which are built up from standard nucleobases and a phosphorylated 1, 5-anhydrohexitol backbone. The term "LNA" as used herein relates to locked nucleic acids. Typically, a locked nucleic acid is a modified and thus inaccessible RNA nucleotide. The ribose moiety of an LNA nucleotide may be modified with an extra bridge connecting the 2' and 4' carbons. Such a bridge locks the ribose in a 3'-endo structural conformation. The locked ribose conformation enhances base stacking and backbone pre-organization. This is assumed to increase the thermal stability, i.e. melting temperature of the oligonucleotide. The term "ANA" as used herein relates to arabinoic nucleic acids or derivatives thereof. A preferred ANA derivative in the context of the present invention is a 2'-deoxy-2'-fluoro-beta-D-arabinonucleoside (2'F-ANA).

The oligonucleotides are typically provided in a liquid, e.g. aqueous, solution. The solution may comprise or be composed of suitable buffers such as a hybridization buffer, e.g. comprising SSC, NaCl, sodium phosphate, SDS, TE and/or $MgCl_2$.

The "pool of starting oligonucleotides for the preparation of synthetic single guide RNA (sgRNA)" as used herein relates to a group of oligonucleotides which provide features necessary to prepare a pool of synthetic single guide RNAs (sgRNA). In this context the term "synthetic single guide RNA (sgRNA)" or "single guide RNA (sgRNA)" as used herein relates to an artificial or synthetic combination of a crRNA and a tracrRNA sequence of the CRISPR/Cas system as described above. Typically, the sgRNA comprises a target specific sequence which can be used to guide a DNA binding protein towards the binding site. As described in Jinek et al., 2012, Science, 337, 816-821 crRNA and tracrRNA can be combined into a functional species (sgRNA) which fulfills both activities (crRNA and tracrRNA) as mentioned above. For example, nucleotides 1-42 of crRNA-sp2, nucleotides 1-36 of crRNA-sp2 or nucleotides 1-32 of crRNA-sp2 may be combined with nucleotides 4-89 of tracrRNA. Further options for obtaining an sgRNA can be derived from Nowak et al., 2016, Nucleic Acids Research, 44, 20, 9555-9564. For example, an sgRNA may be provided which comprises different forms of an upper stem structure, or in which the spacer sequence is differentially truncated from a canonical 20 nucleotides to 14 or 15 nucleotides. Further envisaged variants include those in which a putative RNAP III terminator sequence is removed from the lower stem. Also envisaged is a variant, in which the upper stem is extended to increase sgRNA stability and enhance its assembly with an sgRNA-guided nucleic acid-binding protein, e.g. Cas protein. According to further embodiments of the present invention, the sequence and form of the sgRNA may vary in accordance with the form or identity of the sgRNA-guided nucleic acid-binding protein, e.g. Cas protein. Accordingly, depending on the original of said sgRNA-guided nucleic acid-binding protein, a different combination of sequence elements may be used. The present invention further envisages any future development in this context and includes any modification or improvement of the sgRNA-nucleic acid-binding protein interaction surpassing the information derivable from Jinke et al., 2012 or Nowak et al., 2016. In specific embodiments, the sgRNA to be used may have the sequence of any one of SEQ ID NO: 1 to 3. Particularly preferred is the use of an *Streptococcus pyogenes* sgRNA, e.g. as used in commercially available kits such as EnGen sgRNA synthesis Kit provided by New England Biolabs Inc. Also envisaged are similar sgRNA forms from other commercial suppliers, or individually prepared sgRNAs. Such sgRNAs may be derived from the sequence of SEQ ID NO: 1 if used with a cognate nucleic acid-binding protein form *S. pyogenes*. Alternatively, the sgRNA may be derived from the sequence of SEQ ID NO: 2 if used with a cognate nucleic acid-binding protein form *Staphylococcus aureus*. In a further alternative, the sgRNA may be derived from the sequence of SEQ ID NO: 3 if used with a cognate nucleic acid-binding protein form *Streptococcus thermophilus*.

The features necessary to prepare a synthetic single guide RNA (sgRNA), in general, comprise all elements which are necessary to generate an sgRNA molecule suitable for employment in a CRISPR/Cas system as described herein above. Accordingly, these features include the presence of a promoter segment; the presence of a random segment as target specific sequence which serves as complementary sequence for a potential binding or hybridization interactor having a matching sequence; and the presence of a binding element which is complementary to at least a portion of a scaffold sequence for interaction with the sgRNA-guided nucleic acid-binding protein. The mentioned features may be provided in any suitable order. It is preferred that the order is, from 5' to 3': (i) promoter segment, (ii) random segment and (iii) biding element for scaffold sequence. The members of said group of oligonucleotides differ by the sequence of the random segment.

The "promoter segment" as used herein relates to any suitable promoter structure, which is capable of initiating RNA transcription. It is preferred that the promoter is a promoter which operates under in vitro conditions. In further embodiments, the promoter may be a constitute promoter or a regulable promoter. An example of a suitable promoter is the T7 RNA polymerase promoter. In alternative embodiments, the promoter may be an U6 RNA polymerase III promoter, a type III RNA polymerase III promoter H1, or a Cytomegalovirus promoter (CMV), preferably a minimal CMV promoter. The promoter segment may be accompanied or additionally comprise further elements such as spacer elements, guiding elements etc. For example, upstream of a spacer sequence of the promoter the segment may preferably comprise 1 or 2 guanine residues. Further details for the promoter segment may be derived from suitable literature sources such as Milligan et al., 1987, Nucleic Acids Research, 15, 21, 8783-8798 or Nowak et al., 2016, Nucleic Acids Research, 44, 20, 9555-9564.

The "random segment" as used herein relates to a nucleic acid stretch comprising random base sequences, which typically cover all sequence possibilities in the covered stretch, including mono-nucleotide stretches such as poly-T, poly-A, poly-G, poly-C. In certain embodiments a majority or a certain amount of possible nucleotide combinations or sequences may be represented by the random segments, e.g. 99%, 95%, 90%, 85%, 80%, 75%, 70% or less or any value in between the mentioned values. In preferred embodiments the random segment comprises between about 10 to 30 random nucleotides, e.g. 10, 11, 12, 13, 14, 15, 16, 17, 18, 19, 20, 21, 22, 23, 24, 25, 26, 27, 28, 29 or 30 nucleotides. It is particularly preferred that the random segment comprises about 20 nucleotides.

The "pool" of oligonucleotides may have any suitable size. Typically, the size of the pool is dependent on the length of the random segment such that a longer sequence implies a bigger pool of oligonucleotides with longer segments necessitating more different oligonucleotides to cover all possible sequence variations than shorter segments. The pool of oligonucleotides may accordingly comprise segments with a random base sequence, i.e. without predefined sequence thus comprising all possible nucleotide combinations or sequences in said segment.

In specific embodiments certain random segments may be overrepresented, while other may be underrepresented. This over- or underrepresentation may be controlled on purpose, e.g. according to necessities, known or expected sequence compositions in a sample or the addition of separation or elimination techniques used during sample preparation, e.g. length exclusions etc. For example, it may be advantageous to provide a higher representation of target specific sequences for nucleic acid species which are present more frequently in a test sample such as rDNA sequences, repetitive sequences etc.

In further embodiments, the pool of oligonucleotides may comprise a one time or several times representation of a single specific nucleotide combination or sequence. For example, each possible nucleotide combination or sequence in the random segment as defined above may be represented in the pool of oligonucleotides 1 time, 2 times, 3 times, 4 times, 5 times, 10 times, 50 times, 100 times, 1000 times or more often.

Figure 2:
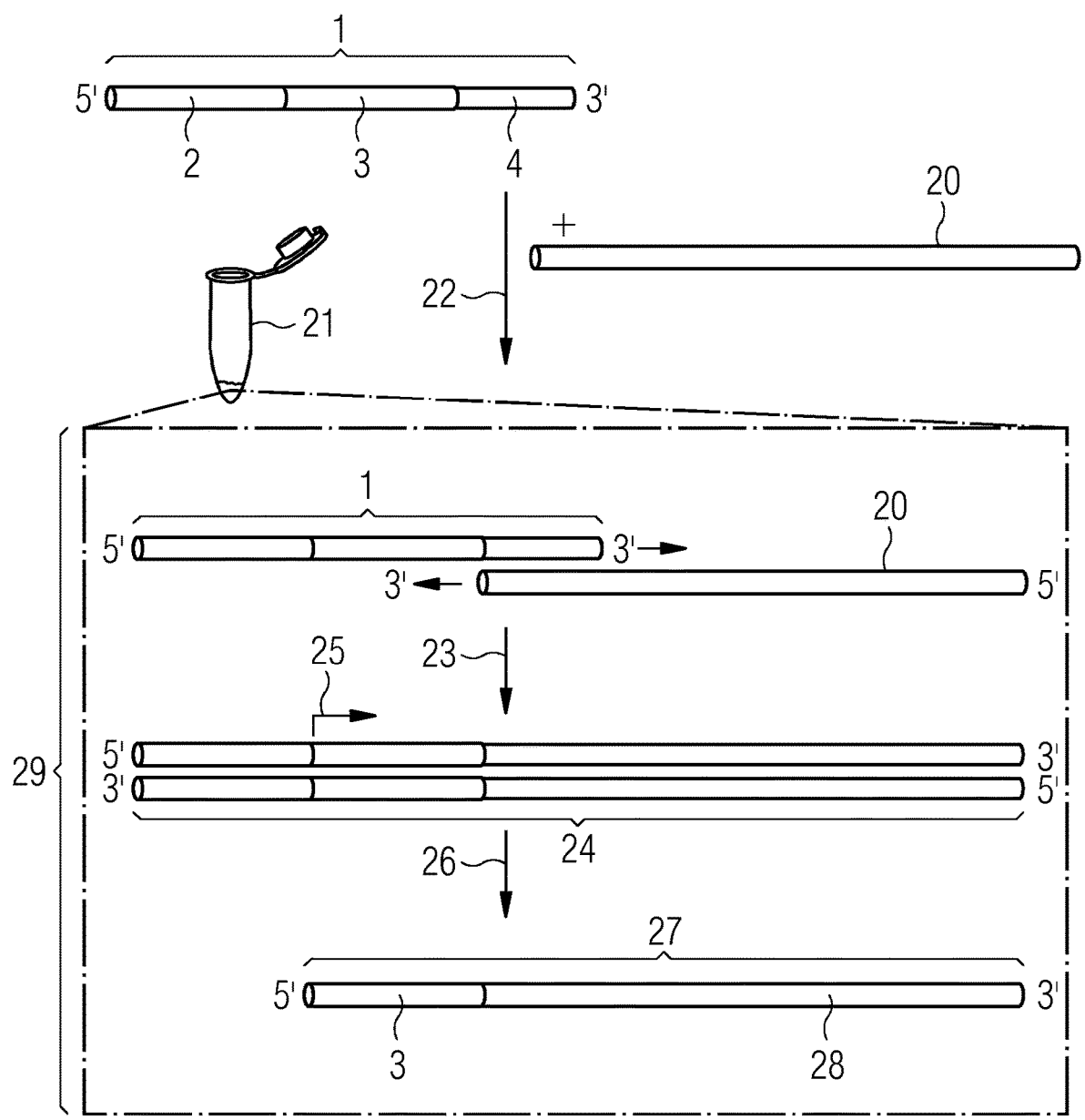
FIG. 2 depicts steps for the preparation of a target-specific sgRNA to be used according to an embodiment of the present invention.

The term "binding element which is complementary to at least a portion of a scaffold sequence for interaction with the sgRNA-guided nucleic acid-binding protein" relates to a nucleic acid segment, which comprises a sequence being complementary to an oligonucleotide comprising crRNA and tracrRNA functionalities as combined in sgRNA, preferably as described herein above, comprising a crRNA repeat motif and an RNA double helix forming element. The term "scaffold sequence" as used herein relates to said structural motifs which are typically required for the binding of and interaction with the sgRNA-guided nucleic acid-binding protein, e.g. Cas protein, as defined above. By providing said scaffold functionality in separate oligonucleotides, a hybridization step between the pool of starting oligonucleotides, preferably a reduced pool of starting oligonucleotides according to the invention, and said scaffold sequence, followed by DNA extension leads to a double stranded template molecule comprising a promoter segment, a random segment as target specific sequence and said sgRNA scaffold functionality in one entity. The process of obtaining said double stranded template molecule comprising a promoter segment, a random segment as target specific sequence and said sgRNA scaffold functionality in one entity, as well as the subsequent step of generating an sgRNA molecule on the basis of said template molecule is schematically depicted in FIG. 2.

The term "complementary" as used herein refers to the presence of matching base pairs in opposite nucleic acid strands. For example, to a nucleotide or base A in a sense strand a complementary or antisense strand binds with a nucleotide or base T, or vice versa; likewise to a nucleotide or base G in a sense strand the complementary or antisense strand binds with a nucleotide or base C, or vice versa. This scheme of complete or perfect complementarity may, in certain embodiments of the invention, be modified by the possibility of the presence of single or multiple non-complementary bases or stretches of nucleotides within the sense and/or antisense strand(s). Thus, to fall within the notion of a pair of sense and antisense strands, both strands may be completely complementary or may be only partially complementary, e.g. show a complementarity of about 80%, 85%, 90%, 91%, 92%, 93%, 94%, 95%, 96%, 97%, 98%, 99%, 99.5%, or 100% between all nucleotides of both strands or between all nucleotides in specific segments as defined herein. Non-complementary bases may comprise one of the nucleotides A, T, G, C, i.e. show a mismatch e.g. between A and G, or T and C, or may comprise any modified nucleoside bases including, for example, modified bases as described in WIPO Standard ST.25. Furthermore, the present invention also envisages complementarity between non-identical nucleic acid molecules, e.g. between a DNA strand and a RNA strand, a DNA strand and a PNA strand, a DNA strand and a CNA strand, etc. It is preferred that the complementarity between strands or segments as defined herein is a complete or 100% complementarity.

The term "complementary to at least a portion of a scaffold sequence" as used herein means that the binding segment has a complementary overlap with said oligonucleotide comprising the scaffold sequence. The overlap may, for example, be an overlap of 5, 7, 10, 12, 15, 18, 20, 22, 25, 28 or 30 nucleotides, or any value in between the mentioned values. Also envisaged are longer overlaps. Preferred are short overlaps in the range of 5 to 20 nucleotides. The length of the overlap may further be adjusted in view of hybridization efficiency. The overlap typically is at the 3' end of the starting oligonucleotide and at the 5' end of the oligonucleotide comprising the scaffold sequence. Within said overlap the matching or complementarity between the complementary bases is preferably 100%. In alternative embodiments, the matching is less than 100%, e.g. 99%, 95%, 90%, 85% or less than 85%.

In a second step one or more sense and/or antisense strand catcher oligonucleotides are provided. The term "sense strand catcher oligonucleotide" as used herein relates to an oligonucleotide of a defined length which is designed to hybridize with and thereby to bind to or to catch a corresponding oligonucleotide out of the pool of starting oligonucleotides as mentioned above, i.e. comprising a corresponding antisense strand (3' to 5' direction). Typically, the sequence of the sense catcher oligonucleotide corresponds to the 5' to 3' sequence of a polynucleotide or, preferably, a portion of a polynucleotide, which should be enriched or should be comprised in an enriched population of target polynucleotides.

The term "antisense strand catcher oligonucleotide" as used herein relates to an oligonucleotide of a defined length which is designed to hybridize with and thereby to bind to or to catch a corresponding oligonucleotide out of the pool of starting oligonucleotides as mentioned above, i.e. comprising a corresponding sense strand (5' to 3' direction). Typically, the sequence of the sense catcher oligonucleotide corresponds to the 3' to 5' sequence of a polynucleotide or, preferably, a portion of a polynucleotide, which should be enriched or should be comprised in an enriched population of target polynucleotides.

For example, the catcher oligonucleotide is complementary to a target polynucleotide or a polynucleotide comprising a target specific sequence as defined herein, e.g. covering a gene, one or more exons of a gene, an intergenic region, a non-transcribed regulatory region, and/or an open reading frame or a sub-portion thereof, or, in further embodiments, covering a panel of different genes, a panel of one or more exons of different genes, a panel of intergenic regions, a panel of non-transcribed regulatory regions, and/or a panel of open reading frames or sub-portions thereof, as well as combinations of the before mentioned elements. It is preferred that panels of genes etc. are covered by groups of catcher oligonucleotides.

In one embodiment both catcher oligonucleotide forms (sense and antisense) may be provided together or at the same time. If both catcher oligonucleotide forms are provided together or at the same time they are provided in a spatially separated manner in order to avoid hybridization between sense and antisense stretches. Alternatively, they may be provided in an immobilized and thus spatially separated form such that a hybridization between the sense and antisense form can be excluded. In alternative embodiments, either a sense or an antisense catcher oligonucleotide is provided first. In such a scenario the invention envisages that either the other catcher oligonucleotide is not used, or alternatively that the other catcher oligonucleotide is used subsequently. In the latter case the method may comprise additional steps of: (iv-a) providing one or more antisense or sense strand catcher oligonucleotides, depending on the previous use of a sense or antisense strand catcher, i.e. if a sense strand catcher oligonucleotide was used in step (ii) and (iii) as defined above in step (iv-a) an antisense strand catcher oligonucleotide may be used; or, vice versa, if an antisense strand catcher oligonucleotide was used in step (ii) and (iii) as defined above, in step (iv-a) an antisense strand catcher oligonucleotide may be used, wherein said catcher oligonucleotides are complementary to at least a portion of the target specific sequence, comprising a tag capable of binding to a cognate interactor; (iv-b) hybridizing the reduced pool of starting oligonucleotides as obtained in step (iv) and said sense or antisense strand catcher oligonucleotide(s); (iv-c) removing complexes of starting oligonucleotides and sense or antisense strand catcher oligonucleotides from said reduced pool of starting oligonucleotides by binding said tag to a cognate interactor, preferably located on a bead or a suitable surface, thereby obtaining a further reduced pool of starting oligonucleotides. It is preferred that said steps are to be performed subsequent to step (iv) as defined above.

The hybridization preferably takes place between said catcher oligonucleotide and at least a portion of the target specific sequence provided in the starting oligonucleotide as defined herein. The binding between these molecules is capable of efficiently removing a starting oligonucleotide with a complementary sequence from the pool of starting oligonucleotides.

Preferably, the catcher oligonucleotide comprises between about 10 to 30 nucleotides, e.g. 10, 11, 12, 13, 14, 15, 16 17, 18, 19, 20, 21, 22, 23, 24, 25, 26, 27, 28, 29 or 30 nucleotides. Also envisaged are longer catcher oligonucleotides. It is particularly preferred that the catcher oligonucleotide comprises 20 nucleotides. The catcher oligonucleotide may further comprise additional elements such as spacer elements, barcoding sequences etc. It is preferred that the catcher oligonucleotide is a single strand DNA molecule. Also envisaged are RNA, PNA, CNA, HNA, LNA or ANA molecules or mixtures thereof as catcher oligonucleotides.

In specific embodiments a group of catcher oligonucleotides is provided, wherein said group covers in a consecutive manner a gene, an exon, an intergenic region, an open reading frame or sub-portion thereof. The term "consecutive" means that the catcher oligonucleotides, when combined, cover the entire sequence of said gene, exon, intergenic region, open reading frame or sub-portion thereof without an overlap, or, in further embodiments, with an overlap of 2, 3, 4, 5, 6, 7, 8, 9, 10, 15, or 20 or more nucleotides between each tiling piece.

In accordance with a specific feature of the catcher oligonucleotide, said catcher oligonucleotide comprises a tag which is capable of binding to a cognate interactor. The interactor-tag binding may advantageously be used to pull said catcher oligonucleotides together with any bound or associated starting oligonucleotide comprising a complementary target sequence from the pool of starting oligonucleotides. Examples of suitable tags and interactors are a biotin tag on the catcher oligonucleotide and a streptavidin interactor provided on a suitable surface, e.g. of a reaction vessel, or on a bead etc. Further examples include a magnetic bead being bound to a catcher oligonucleotide and a magnetic separator attracting said beads, e.g. attached at a surface. Also envisaged are embodiments in which the catcher oligonucleotide is immobilized at a surface or solid phase. Such an immobilization may, for example, be in the form of a column. The solid phase may have any suitable form or structure, e.g. be composed of sepharose. This allows to pass or run starting oligonucleotides as defined above through or over said surface or solid phase and to thereby bind them to the catcher oligonucleotide and thus remove them from the pool.

This activity may, in certain embodiments, be repeated one or several times.

In a subsequent step said pool of starting oligonucleotides and said sense and/or antisense strand catcher oligonucleotide(s) are hybridized. The hybridization typically takes place in a liquid solution, e.g. an aqueous solution comprising a suitable buffer as defined above. The hybridization may be performed in accordance with any suitable temperature, ion concentration and/or pH parameter known to the skilled person. For example, the hybridization may be performed at a temperature and/or pH and/or ionic concentration in the solution at which a complementary base-pairing between most, preferably all complementary bases in the starting oligonucleotide and the sense strand catcher oligonucleotide takes place. Unspecific binding or hybridization reactions may, for example, be avoided by setting the temperature to a value which only allows for a complete, i.e. 100% complementary binding. In alternative embodiments, the temperature may be set to a value, which allows for a complementary binding of about 99%, 98%, 95%, 90%, 85% or 80% of complementary bases.

In a further step of the method of obtaining an enriched population of a target polynucleotide of the present invention complexes of starting oligonucleotides and sense strand catcher oligonucleotides and/or complexes of starting oligonucleotides and antisense strand catcher oligonucleotides are removed from the pool of starting oligonucleotides. The removal is preferably initiated by binding said tag to a cognate interactor, preferably located on a bead or a suitable surface. For example, by introducing beads comprising streptavidin molecules a biotin tag may be associated to said tag. Furthermore, hybridized starting oligonucleotides, i.e. those oligonucleotides which comprise a target sequence matching the sequence of the sense strand catcher oligonucleotide are indirectly also bound to the bead. Subsequently, the beads with the associated nucleic acids can be removed from the solution. For example, the bead may be a magnetic bead which can be removed via magnetic force. Also envisaged are different removal options such as centrifugation or filtration. Alternatively, the removal may be implemented by magnetic beads—magnetic force interaction. In such a scenario the catcher oligonucleotide is linked to a magnetic bead. After hybridization with a matching starting oligonucleotide a magnetic force is applied and the complex between catcher oligonucleotide and starting oligonucleotide can be removed from the solution, e.g. towards a magnetic zone.

After having performed the above outlined step the pool of starting oligonucleotides is reduced, i.e. starting oligonucleotides complementary to the sequence of the sense strand and/or antisense strand catcher oligonucleotide are no longer present in the pool or their presence has been reduced. The term "reduced presence" as used herein means that the number of starting oligonucleotides complementary to the sequence of the sense strand and/or antisense strand catcher oligonucleotide has been reduced 5 fold, 10 fold, 20 fold, 30 fold, 40 fold, 50 fold, 100 fold.

In a specific embodiment the pervious steps (iii) and (iv), i.e. the step of hybridizing the pool of starting oligonucleotides and said sense and/or antisense strand catcher oligonucleotide(s), and the step of removing complexes of starting oligonucleotides as defined above, may be repeated one or several times. For example, these steps may be repeated 1, 2, 3, 4, 5 or more times. The repetition may, in certain embodiments, be connected with an amplification step, e.g. via PCR, of the reduced pool of starting oligonucleotides. Accordingly, a suitable primer binding site on each starting oligonucleotide may be present and be used for the amplification. The amplification may preferably be performed with a Pfu DNA polymerase, or other thermostable DNA polymerase with high fidelity and the corresponding system. Each repetition may be combined with a washing step and or a quality control step. For example, the presence of certain elements in the reduced pool may be determined with real-time PCR. Typically, each repetition is performed with a new catcher oligonucleotide or new group of catcher oligonucleotides. In further embodiments, each repetition may be performed with a different catcher oligonucleotide or a different group of catcher oligonucleotides. The difference may, for example, be a different portion of the overall target sequence, e.g. an adjacent sequence portion of a gene or genomic sequence if said gene is covered by several adjacent or consecutive or partially overlapping catcher oligonucleotides.

In a preferred embodiment during each repetition of method steps (iii) to (iv) one or more sense strand and/or antisense strand catcher oligonucleotide(s) representing one or more different gene(s), exon(s) or open reading frame(s) (ORFs) are used. For example, if more than one gene, exon or ORF is to be covered by said catcher oligonucleotides, each repetition of steps (iii) and (iv) may be performed with another gene-, exon- or ORF-related catcher catcher oligonucleotide. In further embodiments 2, 3, 4, 5, 6 or more genes, exons or ORFs may be covered by catcher oligonucleotides to be used during a repetition of steps (iii) to (iv).

In a further step a pool of sgRNAs with said reduced pool of starting oligonucleotides obtained in step (iv) is generated.

This step may typically be performed as depicted in FIG. 2. Typically, an single stranded oligonucleotide, preferably a DNA molecule, comprising crRNA and tracrRNA functionalities as combined in sgRNA, preferably as described herein above, comprising a crRNA repeat motif and an RNA double helix forming element is hybridized to a starting oligonucleotide obtained in step (iv) via the binding element present as defined herein above, which is present in said starting oligonucleotide. Subsequently, single stranded portions of the hybrid complex may be filled via DNA extension reactions. This reaction is preferably performed with a DNA polymerase, e.g. a T4 DNA polymerase, or Klenow enzyme.

The resulting double stranded template molecule comprising a promoter segment, a random segment as target specific sequence and said sgRNA scaffold functionality in one entity may, in certain embodiments, be amplified, e.g. via PCR. Subsequently, the template can be transcribed into an RNA molecule via the promoter segment as defined herein above, yielding a target-specific sgRNA which can be used for CRISPR/Cas activities.

In a specific embodiment, the pool of sgRNAs is obtained according to a commercial protocol and on the basis of a commercial kit as, for example, provided by New England Biolabs such as the EnGen sgRNA synthesis Kit. Also envisaged are similar sgRNA forms form other commercial suppliers.

Accordingly, in a further aspect, the present invention relates to a method of obtaining such a pool of target-irrelevant synthetic single guide RNAs (sgRNAs) for a sgRNA-guided nucleic acid-binding protein. This method comprises essentially the steps (i) to (v) as defined herein. In an alternative aspect the present invention envisages the provision of a reduced pool of starting oligonucleotides comprising essentially the steps (i) to (iv) as defined herein above.

In certain embodiments, the sgRNA obtained after step (v) may be stored, modified and/or purified in order to allow for a suitable further usage. For example, potentially present 5' triphosphate residues may be removed, e.g. by employing alkaline phosphatase. A purification of the sgRNA may be performed according to any suitable protocol known to the skilled person, e.g. with a spin column to remove proteins, salts and nucleotides. Also envisaged is, in certain embodiments, a quality check of the sgRNA before further usage, e.g. via UV light absorbance at 260 nm.

In a further step of the method of obtaining an enriched population of a target polynucleotide of the present invention a mixture of polynucleotides obtained from a test sample is cleaved with an sgRNA-guided nucleic acid-binding protein using the pool of sgRNAs obtained in step (v) as defined above.

The term "test sample" as used herein relates to any biological material obtained via suitable methods known to the person skilled in the art from a subject. The sample used in the context of the present invention should preferably be collected in a clinically acceptable manner, more preferably in a way that nucleic acids are preserved. The biological samples may include body tissues and/or fluids, such as blood, or blood components like serum or plasma, sweat, sputum or saliva, semen and urine, as well as feces or stool samples. Furthermore, the biological sample may contain a cell extract derived from or a cell population including an epithelial cell, preferably a neoplastic epithelial cell or an epithelial cell derived from tissue suspected to be neoplastic.

Particularly preferred are samples of cancerous tissue or comprising cancer cells. Alternatively, the biological sample may be derived from the environment, e.g. from the soil, a lake, a river etc., or from animal sources. In certain embodiments cells may be used as primary sources for polynucleotides. Accordingly, the cells may be purified from obtained body tissues and fluids if necessary, and then further processed to obtain polynucleotides. In certain embodiments samples, in particular after initial processing, may be pooled. The present invention preferably envisages the use of non-pooled samples. In a specific embodiment of the present invention the content of a biological sample may also be submitted to a specific pre-enrichment step. For instance, a sample may be contacted with ligands specific for the cell membrane or organelles of certain cell types, functionalized for example with magnetic particles. The material concentrated by the magnetic particles may subsequently be used for the extraction of polynucleotides. In further embodiments of the invention, biopsy or resections samples may be obtained and/or used. Such samples may comprise cells or cell lysates. Furthermore, cells, e.g. tumor cells, may be enriched via filtration processes of fluid or liquid samples, e.g. blood, urine, sweat etc. Such filtration processes may also be combined with pre-enrichment steps based on ligand specific interactions as described herein above.

The term "mixture of polynucleotides" as used herein relates to nucleic acids derived from a sample as mentioned above. The polynucleotide to be use in accordance with the present invention is preferably a DNA molecule or a cDNA molecule. The cDNA molecule may be obtained in accordance with any suitable methodology, e.g. by reverse transcription. The DNA molecule may be a genomic DNA or a derivative thereof. Also envisaged is the use of DNA libraries.

In preferred embodiments, mixture of polynucleotides obtained from a test sample comprises genomic DNA and/or cDNA molecules whose size is optionally adjusted to a predefined value. For example, a mixture of polynucleotides may comprise genomic DNA or cDNA molecules which are sheared or fragmented in accordance with any suitable protocol known to the skilled person. Such methods include a restriction digest, adaptive focused acoustic shearing (AFA) or Covaris shearing, use of nebulization forces, sonication, point-sink shearing or the use of a French press shearing procedure. It is preferred to use acoustic shearing, in particular the Covaris shearing. In an optional embodiment, the size of the polynucleotides obtained may be adjusted to a predefined range. Exemplary ranges are about 2 kb to 2.5 kb, 2.5 kb to 3 kb, or 3 kb to 3.5 kb etc., 5 kb to 6 kb, 10 kb to 12 kb etc. The size of the polynucleotides, as well as any optional adjustment, may depend on the target sequence length as mentioned herein.

The cleavage with an sgRNA-guided nucleic acid-binding protein, e.g. a nuclease such as Cas, using the pool of sgRNAs obtained in step (v) is performed according to the CRSIPR/Cas method as described above. Typically, the mixture of polynucleotides as defined above is added to a reaction solution comprising the sgRNA as mentioned above in a suitable concentration, a suitable reaction buffer and an sgRNA-guided nucleic acid-binding protein in a suitable concentration. The reaction may be incubated at a suitable temperature. Subsequently, the reaction may, in certain embodiments, be stopped by the addition of a proteinase, e.g. proteinase K or, preferably, by performing a heat denaturation step, e.g. at 65° C.

In a specific embodiment, the cleavage may also be performed according to a commercial protocol and on the basis of a commercial kit as, for example, provided by New England Biolabs such as the EnGen Cas9 NLS, *S. pyogenes* in vitro digestion kit. Also envisaged are similar digestion protocols form other commercial suppliers.

In a final step of the method of obtaining an enriched population of a target polynucleotide of the present invention a size selection is performed which allows to separate uncut target polynucleotides from cleaved polynucleotides as obtained in step (vi). Typically, due to the use of a random target sequence for the sgRNA preparation, polynucleotide molecules comprising a matching random sequence are cleaved with the CRSIPR/Cas system. Polynucleotide molecules which comprise a target specific sequence, which is not recognized by the sgRNAs in the pool of sgRNAs since these molecules have been removed via the hybridization with the catcher oligonucleotide as described above, will not be cleaved and accordingly have a larger size. The size selection can be performed with any suitable method. For example, an agarose gel- or polyacrylamide gel-based approach or a bead based approach may be used. In preferred alternative embodiments magnetic beads may be used to remove short fragments.

Obtained target polynucleotides, i.e. polynucleotides comprising a target specific sequence, may subsequently be purified, stored and/or used for additional activities.

In a specific embodiment of the present invention, one additional activity to be performed with said polynucleotides is the sequencing said obtained target polynucleotide. The term "sequencing" as used herein relates to any suitable sequencing methodology known to the skilled person. Preferably, a next-generation sequence (NGS) or second generation sequencing technique may be used, which is usually a massively parallel sequencing approach performed in a highly parallel fashion. The sequencing may, for example, be performed according to parallel sequencing approach on platforms such as Roche 454, GS FLX Titanium, Illumina, Life Technologies Ion Proton, Oxford Nanopore Technologies, Solexa, Solid or Helicos Biosciences Heliscope systems.

The sequencing may, in certain embodiments, also include an additional preparation of polynucleotides, the sequencing, as well as subsequent imaging and initial data analysis steps.

Preparation steps may, for example, include randomly breaking polynucleotides into smaller sizes and generating sequencing templates such as fragment templates. Spatially separated templates can, for example, be attached or immobilized at solid surfaces which allows for a sequencing reaction to be performed simultaneously. In typical examples, a library of nucleic acid fragments is generated and adaptors containing universal priming sites are ligated to the end of the fragments. Subsequently, the fragments are denatured into single strands and captured by beads. After amplification a huge number of templates may be attached or immobilized in a polyacrylamide gel, or be chemically crosslinked to an amino-coated glass surface, or be deposited on individual titer plates. Alternatively, solid phase amplification may be employed. In this approach forward and reverse primers are typically attached to a solid support. The surface density of amplified fragments is defined by the ratio of the primers to the template on the support. This method may produce millions of spatially separated template clusters which can be hybridized to universal sequencing primers for massively parallel sequencing reactions. Further suitable options include multiple displacement amplification methods. Suitable sequencing methods include, but are not limited to, cyclic reversible termination (CRT) or sequencing by synthesis (SBS) by Illumina, sequencing by ligation (SBL), single-molecule addition (pyrosequencing) or real-time sequencing. Exemplary platforms using CRT methods are Illumina/Solexa and HelicoScope. Exemplary SBL platforms include the Life/APG/ SOLiD support oligonucleotide ligation detection. An exemplary pyrosequencing platform is Roche/454. Exemplary real-time sequencing platforms include the Pacific Biosciences platform and the Life/Visi-Gen platform. Other sequencing methods to obtain massively parallel nucleic acid sequence data include nanopore sequencing, sequencing by hybridization, nano-transistor array based sequencing, scanning tunneling microscopy (STM) based sequencing, or nanowire-molecule sensor based sequencing. Further details with respect to the sequencing approach would be known to the skilled person, or can be derived from suitable literature sources such as Goodwin et al., 2016, Nature Reviews Genetics, 17, 333-351, van Dijk et al., 2014, Trends in Genetics, 9, 418-426 or Feng et al., 2015, Genomics Proteomics Bioinformatics, 13, 4-16.

In a further aspect the present invention relates to a target polynucleotide obtainable by the method of obtaining an enriched population of a target polynucleotide as defined herein above. The target polynucleotide may accordingly be present in a mixture with non-target polynucleotides, e.g. in a size fractionable state. Accordingly, by separating the target polynucleotide from non-target polynucleotides as described herein a pure fraction of target polynucleotides may be obtained. Similarly, the target polynucleotide may be present in a separated form in gel such as an agarose gel or polyacrylamide gel and can thus be extracted therefrom with suitable methods known to the skilled person. The target polynucleotide obtained may be purified, stored or modified according to any suitable approach. The target polynucleotide may be provided in any suitable buffer or liquid, or it may be provided in dried or lyophilized form.

In a further aspect the present invention relates to a pool of target-irrelevant synthetic single guide RNAs (sgRNAs) for a sgRNA-guided nucleic acid-binding protein, e.g. Cas9, obtained according to a method of the present invention. The pool may accordingly be provided as RNA molecule. It is preferred that the RNA has been purified and/or cleaned. It may be provided in any suitable buffer or liquid, or may be provided in dried or lyophilized form. In an alternative embodiment, the pool of sgRNAs is provided as reduced pool of starting oligonucleotides in accordance with the present invention. In a further example, it may be provided as mixture of starting oligonucleotides and scaffold sequence containing oligonucleotides as described above.

In a further aspect the present invention relates to a kit comprising a pool of sgRNAs obtainable by the method of obtaining a pool of target-irrelevant synthetic single guide RNAs (sgRNAs) for a sgRNA-guided nucleic acid-binding protein and a sgRNA-guided nucleic acid-binding protein. The kit is preferably for enriching a population of a target polynucleotide. The features of the methods as defined herein above apply also to the kit of the present invention. The kit may, for example, comprise reagents and components as defined in one or more steps of the present methods. For example, the kit may comprise reagents or components for cleaving a mixture of polynucleotides obtained from a test sample with an sgRNA-guided nucleic acid-binding protein. In a different embodiment, the kit may comprise or may comprise in addition reagents or components for performing a size selection. The kit may, in general, comprise suitable buffer solutions, labels or washing liquids etc. Furthermore, the kit may comprise an amount of a known nucleic acid molecule or protein, which can be used for a calibration of the kit or as an internal control. Corresponding ingredients would be known to the skilled person.

Additionally, the kit may comprise an instruction leaflet and/or may provide information as to its usage etc.

Also envisaged is an apparatus performing the above mentioned method steps. The apparatus may, for example, be composed of different modules which can perform one or more steps of the method of the present invention. These modules may be combined in any suitable fashion, e.g. they may be present in a single place or be separated. Also envisaged is the performance of the method at different points in time and/or in different location. Some steps of the method as define herein may be followed by breaks or pauses, wherein the reagents or products etc. are suitably stored, e.g. in a freezer or a cooling device. In case these steps are performed in specific modules of an apparatus as defined herein, said modules may be used as storage vehicle. The modules may further be used to transport reaction products or reagents to a different location, e.g. a different laboratory etc.

In yet another aspect the present invention relates to the use of a pool of sgRNAs obtainable by the method of obtaining a pool of target-irrelevant synthetic single guide RNAs (sgRNAs) for a sgRNA-guided nucleic acid-binding protein for the removal of target-irrelevant polynucleotides from a mixture of polynucleotides in a sgRNA-guided nucleic acid-binding protein-based assay. The assay may comprise the step of cleaving a mixture of polynucleotides obtained from a test sample with an sgRNA-guided nucleic acid-binding protein wherein said nucleic acid-binding protein is guided towards the sequence to be cleaved by the sgRNA obtained in accordance with the methods of the present invention. The features of the methods as defined herein above apply also to the use or assay as mentioned above.

In preferred embodiments of the above mentioned methods, kits or uses the sgRNA-guided nucleic acid-binding protein is a DNA binding Cas protein. Examples of such DNA binding Cas proteins are Cas2, Cas3, Cas5, Csn1 or Csx12 or Cas9. Also envisaged are derivatives thereof or mutants. In particularly preferred embodiments, the sgRNA-guided nucleic acid-binding protein is derived from a family of Cas9 proteins or derivatives thereof. It is even more preferred that the sgRNA-guided nucleic acid-binding protein is Cas9 or a derivative thereof. The derivative is preferably a functional derivative which has a nuclease activity. The present invention further envisages the use of Cas9 derived from different bacterial sources. For example, the Cas9 protein may be derived from *Streptococcus pyogenes, Staphylococcus aureus*, or *Streptococcus* thermophiles. It is preferred that the Cas9 is a *Streptococcus pyogenes* Cas9 protein. Further details on the form and use of Cas proteins may be derived from suitable literature sources such as Jiang and Doudna, 2017, Annu. Rev. Biophys., 46, 505-529, Makarova et al., 2011, Biology Direct, 6, 38 or Wang et al., 2016, Annu. Rev. Biochem., 85, 22.1-22.38.

Turning now to FIG. 1, a schematic illustration of the steps for obtaining a pool of target-irrelevant synthetic single guide RNAs (sgRNAs) according to an embodiment of the present invention is provided. In a first step a pool of starting oligonucleotides 1 comprising a promoter segment 2, a random segment as target specific sequence 3 and a binding segment 4, which is complementary to at least a portion of a scaffold sequence for interaction with the sgRNA-guided nucleic acid-binding protein is provided.

The pool of starting oligonucleotides 1 is hybridized 8 with a sense strand catcher oligonucleotide 5 comprising a tag 6 and a segment 7 which is complementary to the random segment 3. Subsequently, complexes of the starting oligonucleotide 1 and the sense strand catcher oligonucleotide 5 are removed 9 from the solution or reaction mix. Within the solution or reaction mix a reduced pool of starting oligonucleotides 10 is kept. In a subsequent step the reduced pool of starting oligonucleotide 1 is hybridized 8 with an antisense strand catcher oligonucleotide 11 comprising a tag 6 and a antisense strand segment 12 which is complementary to the random segment 3. Then, complexes of the starting oligonucleotide 1 and the antisense strand catcher oligonucleotide 11 are removed 9 from the solution or reaction mix. Within the solution or reaction mix a further reduced pool of starting oligonucleotides 13 is kept.

FIG. 2 shows a schematic illustration of steps for the preparation of a target-specific sgRNA 27 to be used according to an embodiment of the present invention. The method starts with a pool of starting oligonucleotides 1 comprising a promoter segment 2, a random segment as target specific sequence 3 and a binding segment 4, which is complementary to at least a portion of a scaffold sequence for interaction with the sgRNA-guided nucleic acid-binding protein, which is hybridized 22 with a scaffold oligonucleotide 20. The subsequent reaction steps 29 take place in single tube 21. After the hybridization single stranded regions are filled in a DNA extension reaction 23 providing a double stranded DNA molecule 24. In a next step the dsDNA molecule is transcribed 26 starting via promoter activity 25. This yields a target specific sgRNA molecule 27 comprising a target specific sequence 3 and a sgRNA scaffold segment 28.

LIST OF REFERENCE NUMERALS

1 Pool of starting oligonucleotides
2 Promoter segment
3 Random segment as target specific sequence
4 Binding segment
5 Sense strand catcher oligonucleotide
6 Tag
7 Segment which is complementary to the random segment
8 Hybridization reaction
9 Removal of complex from solution
10 Continuation with reduced pool of starting oligonucleotides
11 Antisense strand catcher oligonucleotide
12 Antisense strand segment which is complementary to the random segment
13 Continuation with further reduced pool of starting oligonucleotides
30 Scaffold oligonucleotide
21 Single tube reaction
22 Hybridization reaction with scaffold oligonucleotide
23 DNA extension reaction
24 Double stranded DNA molecule
25 Promoter activity
26 Transcription reaction
27 Target specific sgRNA molecule
28 sgRNA scaffold segment The following figures are provided for illustrative purposes. It is thus understood that the figures are not to be construed as limiting. The skilled person in the art will clearly be able to envisage further modifications of the principles laid out herein.

The invention claimed is:

1. A method of obtaining an enriched population of a target polynucleotide comprising:
   (i) hybridizing
      (a) a pool of starting oligonucleotides, each starting oligonucleotide comprising, in 5' to 3' direction, a promoter segment, a random segment, and a binding segment, wherein the binding segment is complementary to at least a portion of a scaffold oligonucleotide for interaction with a single guide RNAs (sgRNA) nucleic acid-binding CAS protein, and
      (b) one or more sense or antisense strand catcher oligonucleotides, which are complementary to at least a portion of the random segment and comprise a tag;
   (ii) removing complexes of starting oligonucleotides and sense strand catcher oligonucleotides or complexes of starting oligonucleotides and antisense strand catcher oligonucleotides from said pool of starting oligonucleotides by binding said tag to a cognate interactor, thereby obtaining a reduced pool of starting oligonucleotides;
   (iii) preparing a pool of target-irrelevant synthetic sgRNAs for a nucleic acid-binding Cas protein with said reduced pool of starting oligonucleotides obtained in step (ii) by hybridizing the portion of the scaffold oligonucleotides to the binding segment of the reduced pool of the starting oligonucleotides and performing DNA extension reaction followed by DNA transcription from the promoter segment, thereby obtaining the pool of the target-irrelevant synthetic sgRNAs for a nucleic acid-binding Cas protein, wherein the target-irrelevant synthetic sgRNAs comprise the binding segment and a sgRNA scaffold oligonucleotide segment;
   (iv) cleaving a mixture of polynucleotides obtained from a test sample with a sgRNA-guided DNA binding Cas protein using the pool of the target-irrelevant synthetic sgRNAs for a nucleic acid-binding Cas protein obtained in step (iii) to obtain a mixture of cut and uncut polynucleotides; and
   (v) size selecting uncut polynucleotides from said mixture of cut and uncut polynucleotides obtained in step (iv), wherein the target polynucleotide comprises the sequence of the sense strand catcher oligonucleotide or the antisense strand catcher oligonucleotide, thereby obtaining the enriched population of the target polynucleotide.

2. The method of claim 1, wherein the DNA binding Cas protein is a member of the family of Cas9 proteins.

3. The method of claim 1, wherein said random segment comprises between about 10 to 30 random nucleotides.

4. The method of claim 1, wherein said catcher oligonucleotide between about 10 to 30 nucleotides.

5. The method of claim 1, wherein said tag is biotin and wherein said cognate interactor is streptavidin.

6. The method of claim 1, wherein steps (i) and (ii) are repeated 1, 2, 3, 4, 5 or more times.

7. The method of claim 1, wherein said target polynucleotide is selected from the group consisting of a gene, one or more exons of a gene, an intergenic region, a non-transcribed regulatory region, an open reading frame or a sub-portion thereof; a panel of different genes, a panel of one or more exons of different genes, a panel of intergenic regions, a panel of non-transcribed regulatory regions, a panel of open reading frames or sub-portions thereof, and any combination of any of the before mentioned elements.

8. The method of claim 6, wherein during each repetition of method steps (i) and (ii) one or more catcher oligonucleotide(s) representing one or more different gene(s), exon(s) or open reading frame(s) are used.

9. The method of claim 1, wherein said mixture of polynucleotides obtained from a test sample comprises genomic DNA or cDNA molecules whose size is optionally adjusted to a predefined value.

10. The method of claim 1, additionally comprising as step (vi) a step of sequencing said size selected uncut target polynucleotide(s).

11. The method of claim 1, wherein the cognate interactor is located on a bead or a suitable surface.

12. The method of claim 1, wherein the DNA binding Cas protein is a Cas9 protein or a derivative thereof.

13. The method of claim 1, wherein said random segment comprises 20 random nucleotides.

14. The method of claim 1, wherein said catcher oligonucleotide comprises 20 nucleotides.

15. A method of obtaining a pool of target-irrelevant synthetic single guide RNAs (sgRNAs) for a sgRNA-guided nucleic acid-binding Cas protein comprising:
(i) hybridizing
  (a) a pool of starting oligonucleotides, each starting oligonucleotide comprising, in 5' to 3' direction, a promoter segment, a random segment, and a binding segment, wherein the binding segment is complementary to at least a portion of scaffold oligonucleotide for interaction with the sgRNA-guided nucleic acid-binding protein, and
  (b) one or more sense or antisense strand catcher oligonucleotides which are complementary to at least a portion of the random segment and comprise a tag;
(ii) removing complexes of starting oligonucleotides and sense strand catcher oligonucleotides or complexes of starting oligonucleotides and antisense strand catcher oligonucleotides from said pool of starting oligonucleotides by binding said tag to a cognate interactor, thereby obtaining a reduced pool of starting oligonucleotides; and
(iii) preparing a pool of target-irrelevant sgRNAs for a nucleic acid-binding Cas protein with said reduced pool of starting oligonucleotides obtained in step (ii) by hybridizing the portion of the scaffold oligonucleotides to the binding segment of the reduced pool of the starting oligonucleotides and performing DNA extension reaction followed by DNA transcription from the promoter segment, thereby obtaining the pool of the target-irrelevant sgRNAs for a nucleic acid-binding Cas protein comprising the binding segment and a sgRNA scaffold oligonucleotide segment.

16. The method of claim 1, wherein the target polynucleotide comprises the sequence of the sense strand catcher oligonucleotide.

17. The method of claim 1, wherein the target polynucleotide comprises the sequence of the antisense strand catcher oligonucleotide.

18. The method of claim 15, wherein the nucleic acid-binding Cas protein is a DNA binding Cas protein comprising a member of the family of Cas9 proteins.

19. The method of claim 15, wherein said random segment comprises between about 10 to 30 random nucleotides.

20. The method of claim 15, wherein said catcher oligonucleotide comprises between about 10 to 30 nucleotides.

21. The method of claim 15, wherein said tag is biotin and wherein said cognate interactor is streptavidin.

22. The method of claim 15, wherein steps (i) and (ii) are repeated 1, 2, 3, 4, 5 or more times.

23. The method of claim 15, wherein said target polynucleotide is selected from the group consisting of a gene, one or more exons of a gene, an intergenic region, a non-transcribed regulatory region, an open reading frame or a sub-portion thereof; a panel of different genes, a panel of one or more exons of different genes, a panel of intergenic regions, a panel of non-transcribed regulatory regions, a panel of open reading frames or sub-portions thereof, and any combination of any of the before mentioned elements.

24. The method of claim 22, wherein during each repetition of method steps (i) and (ii) one or more catcher oligonucleotide(s) representing one or more different gene(s), exon(s) or open reading frame(s) are used.

25. The method of claim 15, wherein the cognate interactor is located on a bead or a suitable surface.

26. The method of claim 18, wherein the DNA binding Cas protein is a Cas9 protein or a derivative thereof.

27. The method of claim 15, wherein said random segment comprises 20 random nucleotides.

28. The method of claim 15, wherein said catcher oligonucleotide comprises 20 nucleotides.

* * * * *